United States Patent [19]

Bochis

[11] 4,154,835

[45] May 15, 1979

[54] ANTHELMINTIC IMIDAZO [1,2-a] PYRIDINES

[75] Inventor: Richard J. Bochis, East Brunswick, N.J.

[73] Assignee: Merck & Co., Inc., Rahway, N.J.

[21] Appl. No.: 841,260

[22] Filed: Oct. 12, 1977

[51] Int. Cl.$^2$ .................... C07C 471/04; A61K 31/44
[52] U.S. Cl. ................................. 424/256; 546/121; 546/311; 546/314; 546/324; 546/326; 546/346; 546/350
[58] Field of Search ........ 260/295 K, 296 B, 290 HL, 260/295 F; 424/256

[56] References Cited

U.S. PATENT DOCUMENTS

| | | | |
|---|---|---|---|
| 3,701,780 | 10/1972 | Fisher | 260/294.8 C |
| 4,064,239 | 12/1977 | Mrozik | 260/347.2 |

FOREIGN PATENT DOCUMENTS 2655681  6/1977  Fed. Rep. of Germany.

*Primary Examiner*—Natalie Trousof
*Assistant Examiner*—Richard A. Schwartz
*Attorney, Agent, or Firm*—David L. Rose; Harry E. Westlake

[57] ABSTRACT

Novel substituted imidazo [1,2-a] pyridine compounds are disclosed which have a high degree of anthelmintic activity. The compounds are substituted with a carbamate and a halogenated alkene group. Processes for the preparation of such compounds are also disclosed as well as compositions which use the described compounds as active ingredients for the treatment of helminthiasis.

6 Claims, No Drawings

ANTHELMINTIC IMIDAZO [1,2-A] PYRIDINES

SUMMARY OF THE INVENTION

This invention is concerned with certain substituted imidazo [1,2-a] pyridines in which the 2-position is substituted with a carbamate group and the 6-position is substituted with a halogenated unsaturated alkyl group. Thus it is an object of the instant invention to describe such compounds. It is a further object of this invention to describe processes for the preparation of such compounds. A still further object is to describe methods and compositions using such compounds as the active ingredient thereof. Further objects will become apparent from a reading of the following description.

DESCRIPTION OF THE INVENTION

The instant invention is concerned with derivatives of imidazo [1,2-a] pyridine. The structure and numbering of the imidazo [1,2-a] pyridine to be used in the instant application is as follows:

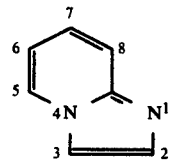

The compounds of the instant invention are imidazo [1,2-a] pyridines which have been substituted on the 2 and 6 positions:

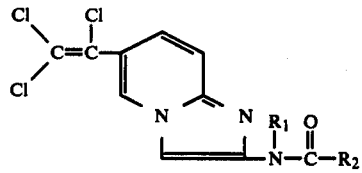

(I)

wherein $R_1$ is hydrogen or loweralkyl; and $R_2$ is loweralkoxy or loweralkyl; and the pharmaceutically acceptable acid addition salts thereof.

The preferred compounds of the instant invention are those wherein $R_1$ is hydrogen and $R_2$ is methoxy or methyl. It is still more preferred that $R_2$ be methoxy.

The compounds of this invention are prepared from an appropriately substituted 2-amino pyridine compound as shown in the following reaction scheme:

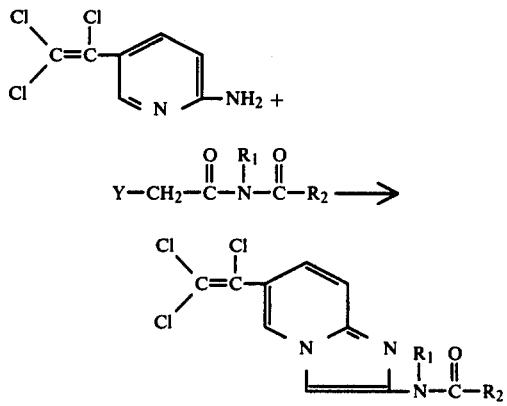

wherein $R_1$ and $R_2$ are as previously defined and y is a halogen selected from chlorine, bromine and iodine. Chlorine is the preferred halogen.

The reactants are combined in a solvent which for optimum results should be a polar aprotic solvent. Suitable solvents are: acetonitrile, dimethylformamide, hexamethylphosphoramide, dimethylacetamide, dimethoxyethane, and the like. The reaction may be conducted at from 50° to 150° C. over a period of from 1 to 50 hours, however, it is preferred to heat the reaction at from 75° to 100° C. for from 1 to 24 hours. The reaction product is isolated by techniques known to those skilled in this art.

The 2-amino-5-trichlorovinyl pyridine starting material (II) is prepared in a series of reactions starting with 2-methyl-5-ethynyl pyridine as outlined in the following reaction scheme:

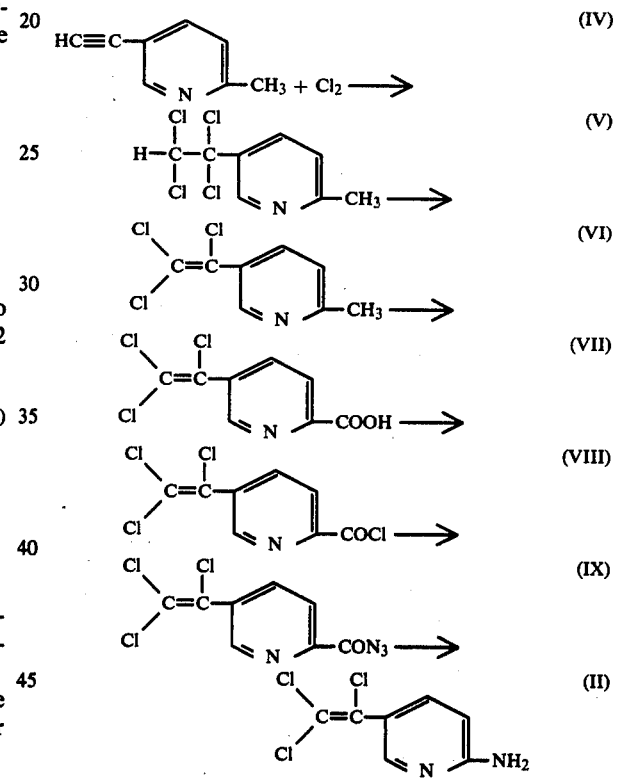

In the first step of the reaction sequence 2-methyl-5-ethynyl pyridine (IV) is treated with chlorine dissolved in a halogenated hydrocarbon at from 0° to 30° C. for from 1 to 4 hours. The preferred solvent is carbon tetrachloride. The tetrachloro compound (V) thus produced is then treated with a base, either organic or inorganic in a solvent to produce the 2-methyl-5-trichlorovinyl compound (VI). The reaction is carried out at from 0° C. to room temperature and is complete in from 10 minutes to 2 hours. The bases which may employed may be organic, such as tertiary amines, such as triethylamine or other trialkylamines; or inorganic such as alkali metal hydroxides or alkoxides. The preferred alkali metals are sodium and potassium. Any solvent which is non-reactive to the reagents employed may be used for this reaction such as water, alcohols or other polar organic solvents. The product (VI) is isolated using standard techniques.

The methyl group of 2-methyl-5-trichlorovinyl pyridine (VI) is then oxidized to a carboxylic acid group using a strong oxidizing agent such as selenium dioxide (SeO₂), sodium dichromate (Na₂Cr₂O₇) potassium permanganate (KMnO₄), and the like. It is preferred to conduct the reaction using selenium dioxide in dioxane. However, the other oxidizing agents may also be carried out in aqueous medium. The reaction is carried out at from room temperature to the reflux temperature of the reaction mixture and is complete in from about 1 to 10 hours.

The carboxylic acid compound (VII) is then treated with thionyl chloride to prepare the acid chloride (VIII). Excess thionyl chloride is generally employed without a solvent and the reaction mixture is heated at reflux temperature for from ½ to 3 hours. The product is isolated using known techniques.

The acid chloride (VIII) is converted to 5-trichlorovinyl pyridine-2-carboxylic acid azide (IX) by treatment with an alkali metal azide at from about 0° C. to room temperature for from 10 minutes to 2 hours. The reaction is carried out in an inert solvent which generally has a slight amount of water added thereto in order to facilitate dissolving the alkali metal azide. Solvents such as acetone, benzene, dioxane, tetrahydrofuran and the like are acceptable. The product is isolated using known techniques.

The carboxylic acid azide compound (IX) is then heated in the presence of acetic acid at about 100° C. until nitrogen evolution stops. This is generally complete in about ½ to 4 hours. The reaction is usually carried out in an inert solvent such as water, benzene, toluene, diphenyl ether and the like. Occasionally a slight amount of water is added along with the organic solvent and acetic acid. If water is used as a solvent, the reaction is complete in from about 5 to 30 minutes. The product 2-amino-5-trichlorovinyl pyridine (II) is recovered using known techniques.

When the imidazo [1,2-a] pyridines of this invention are employed for the treatment and control of helminthiasis, the specific means employed for administering the imidazo [1,2-a] pyridines to the animal is not critical and any of the methods now used or available for treating animals infected with or susceptible to infection by helminths are satisfactory. Where it is desired to administer the imidazo pyridine in dry, solid unit dosage form, capsules, boluses or tablets containing the desired amount of imidazo pyridine usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of anthelmintic agent depending upon factors such as the type of host animal to be treated, the severity and type of infection and the weight of the host. For large animals such as sheep, swine and cattle, unit dosages up to 15 gm., containing from 3 to 12 gm., of imidazo pyridine, may be employed. It is usually preferred, however, to employ unit dosages weighing from 5 to 10 gm. containing from 2 to 8 gm. of imidazo pyridine. Boluses as well as smaller size tablets contain various binders and lubricants and are compounded by techniques well-known in the art. Capsules are prepared readily by mixing the active ingredient with a diluent such as starch or lactose and filling into the capsule.

In order to treat infected animals by means of a drench, the substituted imidazo pyridines of this invention are mixed with a suspending agent such as bentonite and the solid mix is added to water just prior to administration. Preferred drench formulations contain from about 5 to 50% by weight of the imidazo pyridine.

The imidazopyridine described herein also may be administered as a component of the feed of the animals or may be dissolved or suspended in the drinking water. Such compositions comprise the imidazo pyridine intimately dispersed in an inert carrier of diluent. By inert carrier, is meant one that will not react with the imidazo pyridine and one that may be administered safely to animals. Preferably, the carrier is one that is, or may be, an ingredient of the animals's ration.

Suitable compositions include feed supplements in which the active ingredient is present in relatively large amounts and which are suitable for addition to the feed either directly or after an intermediate dilution of blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active imidazo pyridines are intimately dispersed throughout the carrier by methods such as grinding, stirring, milling or tumbling. Compositions containing from about 5 to 50% by weight of the imidazo pyridines are particularly suitable as feed additives.

Such supplements are added to the animal feed in an amount to give the finished feed the concentration of imidazo pyridine desired for the treatment and control of helminthiasis. Although the desired concentration of active compounds will vary depending upon the factors previously mentioned as well as upon the particular imidazo pyridine employed, the imidazo pyridine of this invention are usually fed at concentrations of between 0.5 to 2.0% in the feed in order to achieve the desired anthelmintic result.

The imidazopyridines of this invention are effective fungicides in a variety of applications. Accordingly, they may be employed as fungicides by conventional techniques in the protection of plants, soils, fruits, seeds, fur, wood, paint, textiles, cosmetics, leather, tobacco, rope, paper, pulp, plastic, fuel, rubber, food and the like.

It should be understood that the imidazo pyridine compounds may be utilized in diverse formulations, solid, including finely divided powders and granular materials as well as liquid, such as solutions, emulsions, suspensions, concentrates, emulsifiable concentrate, slurries and the like, depending upon the application intended and the formulation media desired. Thus, it will be appreciated that the imidazo pyridines of this invention may be employed to form fungicidally active compositions containing such compounds as essentially active ingredients thereof, which compositions may also include finely divided dry or liquid diluents, extenders, fillers, conditioners and excipients, including various clays, diatomaceous earth, talc and the like, or water and various organic liquids such as lower alkanols, for example ethanol and isopropanol or kerosene, benzene, toluene and other petroleum distillate fractions or mixtures thereof. The quantity of active imidazo pyridines contained in such formulations will vary widely depending upon the particular imidazo pyridines employed and the particular application intended. In general, useful formulations will contain from about 1 to about 95% of the active imidazo pyridines.

It should be understood also that the imidazo pyridines of the invention may be used in combination one with the other as well as with other fungicidally active materials. For instance, the imidazo pyridines disclosed above may be mixed with sorbic acid or its salts, propionic acid or its salts, mycostatin, sodium diacetate, trichomycin, amphotercin, griseofluvin, undecylenic acid, chloroquinadol, 5,7-dichloro-8-hydroxyquinoline (Vioform), sodium o-phenylphenate, o-phenylphenol, biphenyl, chlorinated phenols, sodium benzoate, dehydroacetic acid and its salts or esters of parahydroxybenzoic acid, such as the methyl and propyl ester (parabens) to give added fungicidal effect when used in appropriate concentrations. It is quite clear, too, that the imidazo pyridines of this invention may be used in conjunction with effective anti-bacterial materials in appropriate instances so as to combine the action of each in such a situation as to be particularly useful, for instance, in applications where the presence of bacteria creates undesirable results alongside the detrimental action of fungi. Accordingly, a combination of antifungal and anti-bacterial agents will be useful in the preparation of germicidal soaps, in the production of cosmetics, and in food, such as beer, cheese, or meat and other leather applications.

As fungicides, the imidazo pyridines of the present invention are useful in inhibiting mold growth in fruit such as citrus fruit. The active agent may be applied at any time before consumption and preferably after harvesting. For instance, the anti-fungal may be applied during initial storage, before or after shipping or during final storage before consumption. The imidazo pyridines may be utilized in a number of ways in this regard and may be applied either directly to the fruit in an emulsion, solution, suspension or the like or it may be applied to the fruit container or wrapper. Suitable carriers for the active agents are waxes and other materials presently known in the art.

EXAMPLE 1

2-Methyl-5-(1,1,2,2-tetrachloroethyl) pyridine 1.17 G. (0.010 moles) of 2-methyl-5-ethynyl pyridine is combined with 15 ml. of carbon tetrachloride and cooled to 0° C. in an ice bath. 1.88 G. (1.20 ml., 0.0275 moles) of liquid chlorine is allowed to evaporate into the reaction mixture over a period of approximately 15 minutes. The internal temperature is kept less than 15° C. with continuous stirring and cooling. The reaction mixture is then stirred at room temperature for 2½ hours. 15 Ml. of water is added and the mixture made basic with a solution of saturated sodium bicarbonate and stirred vigorously for 10 minutes. The layers are separated and the aqueous phase extracted twice with chloroform. The combined organic phases are washed once with saturated sodium chloride, dried over magnesium sulfate, and concentrated to dryness in vacuo affording 2.95 g. of a dark liquid. Analysis of the liquid by gas chromatography and mass spectrometry shows the presence predominately of 2-methyl-5-(1,1,2,2-tetrachloroethyl) pyridine and 2-methyl-5-trichlorovinyl pyridine as the major components.

EXAMPLE 2

2-Methyl-5-(1,1,2,2,-tetrachloroethyl) pyridine 17.55 G (0.150 moles) of 2-methyl-5-ethynyl pyridine is combined with 225 ml. of carbon tetrachloride and cooled to 0° C. 26.6 G. (17 ml., 0.375 moles) of liquid chlorine is allowed to evaporate into the reaction mixture over a period of 45 minutes maintaining the temperature at 0° to 10° C. The reaction mixture is stirred for 2¼ hours. An aliquot of the reaction mixture is removed and analyzed by gas chromatography revealing the presence of predominately trichlorovinyl and tetrachloroethyl compounds with a significant amount of the dichlorovinyl compound. Stirring of the reaction mixture is continued for a total of 3 hours and 15 minutes whereupon an additional 4.2 ml. (0.093 moles) of liquid chlorine is introduced and the mixture stirred an additional 60 minutes. 175 Ml. of cold water is added and a stream of nitrogen blown through the reaction mixture to remove any residual chlorine. The combined organic phase is washed with saturated sodium chloride solution, dried over sodium sulfate and evaporated to dryness in vacuo affording 45.6 g. of a yellow liquid. Gas chromatography analysis of the liquid reveals the presence predominately of the trichlorovinyl compound and the tetrachloroethyl compound. The crude materials from Examples 1 and 2 are used without further purification is subsequent steps.

EXAMPLE 3

2-Methyl-5-trichlorovinyl pyridine 2.95 G. (0.010 moles) of the total crude material from Example 1 is dissolved in 30 ml. of ethanolic potassium hydroxide solution (containing 0.015 moles of KOH) and stirred at room temperature for 1¼ hours. The reaction mixture is diluted with 150 ml. of cold water and extracted 4 times with ether. The ether extracts are washed with saturated sodium chloride solution, dried over sodium sulfate and evaporated to dryness in vacuo. Petroleum ether is added to the residue and the mixture evaporated. The residue is again combined with ether, the ether decanted from slight amount of residual water and the ether layer dried over magnesium sulfate and evaporated to dryness in vacuo. The residue is taken up twice more in petroleum ether and evaporated to dryness affording 2.18 g. of a reddish liquid. Gas chromatographic analysis of the liquid shows 2 compounds approximately in the ratio of 3:1. Mass spectrometry reveals the major component to be 2-methyl-5-trichlorovinyl pyridine and the minor component to be the 1,2-dichlorovinyl compound.

EXAMPLE 4

2-Methyl-5-trichlorovinyl pyridine 45.6 G. of the crude material of Example 2 is combined with a small amount of ethanol at 0° C. and added to 16.5 g. of 85% potassium hydroxide (0.25 moles) dissolved at 400 ml. of ethanol. The reaction mixture is stirred at room temperature for 45 minutes and most of the ethanol is removed at 30° C. under vacuum. The residue is diluted with 1200 ml. of water and extracted 4 times with ether. The ether extracts are washed with saturated sodium chloride solution, dried over sodium sulfate and evaporated to dryness in vacuo. The residue is taken up 600 ml. of petroleum ether and concentrated again. The petroleum ether residue is taken up in ether, dried over magnesium sulfate and evaporated to dryness in vacuo affording 29 g. of a dark oil which crystallizes upon standing. The solid material is crystallized from hexane affording 2-methyl-5-trichlorovinyl pyridine m.p. 37°-39° C. Gas chromatographic analysis of the residue indicates the material to be in excess of 90% of 2-methyl 5-trichlorovinyl pyridine with only a small amount of the dichlorovinyl compound. The material from Examples 3 and 4 is used in subsequent steps without further purification.

EXAMPLE 5

5-Trichlorovinyl pyridine-2-carboxylic acid 1.11. G. (0.0050 moles) of 2-methyl 5-trichlorovinyl pyridine is added at room temperature with stirring to 833 mg. (0.0075 moles) of selenium dioxide suspended in 5 ml. of dioxane. The reaction mixture is refluxed for 8 hours and stirred at room temperature overnight. The reaction mixture is filtered through a filtration medium (diatomaceous earth) and the filtration evaporated to dryness in vacuo affording a reddish solid. The solid is taken up in a minimum amount of hot ethyl acetate and filtered. Upon cooling, crystals are obtained which are filtered and washed with ethyl acetate and dried affording 500 mg. of a tan solid with a m.p. of 158°-159° C.

EXAMPLE 6

5-Trichlorovinyl pyridine-2-carboxylic acid 27.9 G. (0.126 moles) of 2-methyl 5-trichlorovinyl pyridine is oxidized with 20.9 g. (0.188 moles) of selenium dioxide and 125 ml. of dioxane following the procedure of Example 5. 13.4 G. of a tan solid with a m.p. of 160°-161° C. is obtained. A second crop is obtained from the filtrate affording an additional 6.30 g. of a tan solid with a m.p. of 156°-157° C. Infrared and nuclear magnetic resonance of the materials indicates a structure of 5-trichlorovinyl pyridine -2-carboxylic acid.

EXAMPLE 7

5-Trichlorovinyl pyridine-2-carboxylic acid chloride 1.02 G. (0.004 moles) of a 5-trichlorovinyl pyridine-2-carboxylic acid is combined with 12 ml. thionyl chloride and refluxed for 90 minutes. The reaction mixture is cooled and evaporated to dryness in vacuo. The residue is taken up in benzene and again concentrated to dryness and repeated affording a tan solid with a m.p. 88°-89° C.

The above reaction is repeated on 12.3 g. of 5-trichlorovinyl pyridine-2-carboxylic acid and 145 ml. of thionyl chloride affording a tan solid with a m.p. 89°-90° C. The crude 5-trichlorovinyl pyridine-2-carboxylic acid chloride are used without further purification in subsequent steps.

EXAMPLE 8

5-Trichlorovinyl pyridine-2-carboxylic acid azide

143 Mg. (0.0022 moles) of sodium azide is dissolved in 0.4 ml. of water and cooled in an ice bath while a solution of 500 mg. (0.0020 moles) of 5-trichlorovinyl pyridine-2-carboxylic acid chloride in 5 ml. of acetone is added over a period of 2 minutes with stirring. The reaction is stirred at room temperature for 30 minutes and diluted with 15 ml. of water affording 420 mg. of tan fluffy solid with a m.p. of 83° C. with decomposition. Infrared and nuclear magnetic resonance reveals a structure in agreement with 5-trichlorovinyl pyridine-2-carboxylic acid azide.

EXAMPLE 9

2Amino-5-trichlorovinyl pyridine 1.40 G. of 5-trichlorovinyl pyridine 2-carboxylic acid azide is suspended in a mixture of 5 ml. of glacial acetic acid and 5 ml. of water. The temperature of the reaction mixture is slowly raised over a period of 15 minutes to 100° C. and maintained at 100° C. for 35 minutes. The reaction mixture is cooled in ice and the supernatant liquid decanted from a hardened oil. The oil is washed with water and the aqueous washings added to the liquid phase. The oil is suspended in water, made basic with 2.5 N sodium hydroxide, and extracted twice with ethyl acetate. The organic layer is dried and evaporated to dryness in vacuo affording 210 mg. of a dark gum. The above aqueous phase is diluted with a small amount of water and filtered. The filtrate is made basic with 25% sodium hydroxide whereupon a solid material precipitates. The solids are filtered and washed with water and dried affording 530 mg. of an off-white solid with a m.p. of 123°-125° C. Infrared analysis, nuclear magnetic resonance and mass spectrometry are in accord with the structure of 2-amino-5-trichlorovinyl pyridine.

EXAMPLE 10

2-Methoxycarbonylamino-6-trichlorovinyl imidazo [1,2-a] pyridine

447 Mg. (0.0020 moles) of 2-amino-5-trichlorovinyl pyridine is combined with 333 mg. (0.0022 moles) of methyl chloroacetyl carbamate suspended in 5.5 ml. 1,2-dimethoxyethane. The reaction mixture is refluxed overnight, an additional 5 ml. of 1,2-dimethoxyethane is added and refluxing continued for an additional 30 hours. The reaction mixture is cooled in ice, and 10 ml. of ether added. A dark gum separates from the reaction mixture followed by some colorless solids. The supernatant liquid is decanted and the insoluble materials washed with ether. The solid materials are suspended in 7 ml. of saturated sodium bicarbonate solution with vigorous stirring and evolution of carbon dioxide. Methylene chloride is added and the mixture stirred vigorously for 10 minutes. The solution is filtered and the insoluble materials washed with water and methylene chloride and dried affording 75 mg. of a tan solid m.p. 223°-224° C. with decomposition. The solid material is recrystallized in ethanol and the crystals obtained washed twice with ethanol and once with ether and dried in air affording 26.6 mg. of a tan solid m.p. 225°-226° C. which is identified by infrared analysis as 2-methoxycarbonylamino 6-trichlorovinyl imidazo [1,2-a] pyridine.

EXAMPLE 11

2-[Ethyl-N-(Methoxycarbonyl)amino]-6-(trichlorovinyl) imidazo [1,2-a] pyridine

A solution of 1.12 g. (0.005 moles) of 2-amino-5-trichlorovinyl pyridine, 0.505 g. (0.05 moles) of methyl-N-ethyl chloroacetyl carbamate in 15 ml. of dimethoxy ethane is heated at reflux temperature for 4 hours. The solvent is then removed in vacuo and the residue triturated with chloroform. The insoluble material is removed by filtration and the filtrate eluted on a column of silica gel. The column is eluted with ethyl acetate affording 2-[ethyl-N-(methoxycarbonyl)amino]-6-(trichlorovinyl) imidazo [1,2-a] pyridine.

EXAMPLE 12

2-(Acetylamino)-6-(trichlorovinyl) imidazo [1,2-a] pyridine 2.23 G. (0.01 moles) of 2 amino-6-trichlorovinyl pyridine and 2.02 g. of N(chloroacetyl) acetamide in 10 ml. of hexamethylphosphoramide is heated at 100° C. for 5 hours. After cooling, the reaction mixture is diluted with water. The solids are collected by filtration washed with water, ethanol and finally methylene chloride to yield 2-(acetylamino)-6-(trichlorovinyl) imidazo [1,2-a] pyridine.

What is claimed is:

1. A compound having the formula:

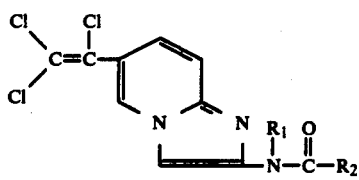

wherein $R_1$ is hydrogen or loweralkyl; and $R_2$ is loweralkoxy or loweralkyl; or a pharmaceutically acceptable acid addition salt thereof.

2. The compound of claim 1 wherein $R_1$ is hydrogen.
3. The compound of claim 2 wherein $R_2$ is methoxy or methyl.
4. The compound of claim 3 which is 2-methoxycarbonylamino-6-trichlorovinyl imidazo [1,2-a] pyridine.
5. The compound of claim 3 which is 2-acetylamino-6-trichlorovinyl imidazo [1,2-a] pyridine.
6. A method for the treatment of helminthiasis which comprises administering to an animal infected with helminthiasis an anthelmintically effective amount of a compound having the formula:

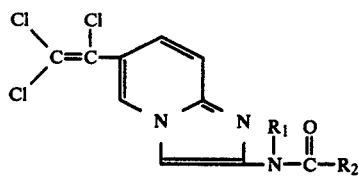

wherein $R_1$ is hydrogen or loweralkyl; and $R_2$ is loweralkoxy or loweralkanol; or a pharmaceutically acceptable salt thereof.

* * * * *